(12) United States Patent
Herrmann et al.

(10) Patent No.: US 11,253,436 B2
(45) Date of Patent: Feb. 22, 2022

(54) METHOD OF MAKING A DENTAL RESTORATION

(71) Applicant: 3M INNOVATIVE PROPERTIES COMPANY, St. Paul, MN (US)

(72) Inventors: Andreas Herrmann, Munich (DE); Michael Jahns, Gilching (DE); Rainer K. Dittmann, Munich (DE); Grit Kindler, Munich (DE); Dajana Maria Anna Zimmermann, Eching am Ammersee (DE)

(73) Assignee: 3M Innovative Properties Company, St. Paul, MN (US)

( * ) Notice: Subject to any disclaimer, the term of this patent is extended or adjusted under 35 U.S.C. 154(b) by 454 days.

(21) Appl. No.: 16/092,626

(22) PCT Filed: Apr. 24, 2017

(86) PCT No.: PCT/US2017/029087
§ 371 (c)(1),
(2) Date: Oct. 10, 2018

(87) PCT Pub. No.: WO2017/189414
PCT Pub. Date: Nov. 2, 2017

(65) Prior Publication Data
US 2019/0117521 A1    Apr. 25, 2019

(30) Foreign Application Priority Data
Apr. 28, 2016   (EP) ..................................... 16167394

(51) Int. Cl.
*A61K 6/822*    (2020.01)
*A61C 13/00*    (2006.01)
(Continued)

(52) U.S. Cl.
CPC ................ *A61K 6/822* (2020.01); *A61C 5/77* (2017.02); *A61C 13/0022* (2013.01);
(Continued)

(58) Field of Classification Search
CPC ................................. A61K 6/818; A61K 6/878
See application file for complete search history.

(56) References Cited

U.S. PATENT DOCUMENTS 5,342,201 A * 8/1994 Oden ........................ A61C 5/20
433/223
2005/0261795 A1 * 11/2005 Ghosh ................ A61C 13/0004
700/118
(Continued)

FOREIGN PATENT DOCUMENTS

| JP | 2016-060687 | 4/2016 |
|----|-------------|--------|
| WO | WO 2009-014903 | 1/2009 |

(Continued)

OTHER PUBLICATIONS

Ritzberger et al, Properties and Clinical Application of Three Types of Dental Glass-Ceramics and Ceramics for CAD-CAM Technologies, Materials, Mar. 2010, 3700-3713 (Year: 2010).*
(Continued)

*Primary Examiner* — Timothy Kennedy

(57) ABSTRACT

A method of making a monolithic dental restoration. The method includes the steps of providing a monolithic precursor of a dental restoration and firing the monolithic dental restoration precursor to provide the monolithic dental restoration. The zirconia material of both the dental restoration precursor as well as the dental restoration has a relative density of greater than 98% of the theoretic density of the zirconia material. The invention helps providing a color of a non-glazed dental restoration which resembles the color of a glazed dental restoration.

11 Claims, 1 Drawing Sheet

(51) Int. Cl.
*A61C 13/083* (2006.01)
*A61C 5/77* (2017.01)
*C04B 35/486* (2006.01)
*A61K 6/818* (2020.01)

(52) U.S. Cl.
CPC ............ *A61C 13/083* (2013.01); *A61K 6/818* (2020.01); *C04B 35/486* (2013.01); *C04B 2235/3224* (2013.01); *C04B 2235/3225* (2013.01); *C04B 2235/3262* (2013.01); *C04B 2235/3272* (2013.01); *C04B 2235/3298* (2013.01); *C04B 2235/608* (2013.01); *C04B 2235/612* (2013.01); *C04B 2235/616* (2013.01); *C04B 2235/6567* (2013.01); *C04B 2235/77* (2013.01); *C04B 2235/9661* (2013.01)

(56) References Cited

U.S. PATENT DOCUMENTS

| | | | |
|---|---|---|---|
| 2006/0025866 A1* | 2/2006 | Serafin, Jr. | ............. B28B 3/003 623/23.56 |
| 2006/0117989 A1 | 6/2006 | Hauptmann | |
| 2013/0224454 A1 | 8/2013 | Jung | |
| 2017/0231730 A1* | 8/2017 | Shen | ............. A61C 13/26 433/201.1 |

FOREIGN PATENT DOCUMENTS

| WO | WO 2009-091552 | 7/2009 |
|---|---|---|
| WO | WO 2010-104901 | 9/2010 |
| WO | WO 2012-036852 | 3/2012 |
| WO | WO 2013-181262 | 12/2013 |
| WO | WO 2014-022643 | 2/2014 |
| WO | WO 2014-046949 | 3/2014 |
| WO | WO 2015-084931 | 6/2015 |

OTHER PUBLICATIONS

Sundh et al, Fracture resistance of yttrium oxide partially-stabilized zirconia all-ceramic bridges after veneering and mechanical fatigue testing, 2005, Dental Materials, 21, pp. 476-482 (Year: 2005).*
International Search Report for PCT International Application No. PCT/US2017/029087, dated Jul. 10, 2017, 5 pages.
European Application 17721495.4 Notice of Opposition dated Aug. 21, 2020.
Ivoclar Vivadent Product Literature for e.MaxZirCAD, 52 pages, Feb. 2010.
Ivoclar Vivadent Product Literature for e.MaxZirCAD, 43 pages, Nov. 2017.
Gernet, W., Bruchfestigkeit von volkeramischen Brucken mit unterschiedlichen Gerustmaterialen, 113 pages, 2010.
Kriegesmann, J., Ultraschallbearbeitung, Fraunhofer Aug. 13, 2020.
Schubert, H., Einfluβ der intergranularen Glasphase auf die Umwandlungsfahigkeit von TZP, Gefugecharakterisierung, Chapter 5.1.3.1, 11 pages.
Mache, Tobias, Frakturstabilitat von Zirkoniumdioxidkronengerusten, 115 pages, 2012.

* cited by examiner

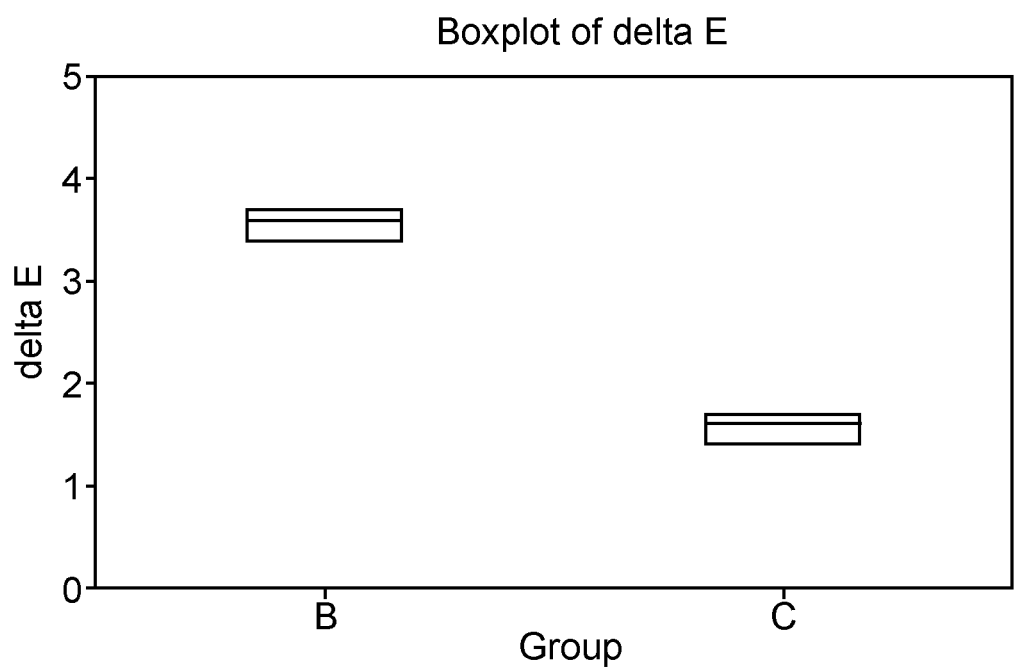

METHOD OF MAKING A DENTAL RESTORATION

FIELD OF THE INVENTION

The invention relates to a method of making a monolithic dental restoration. In particular the invention relates to a method which comprises an additional firing step for providing a color change.

BACKGROUND ART

Dental restorations, in particular larger dental restorations like replacement teeth, crowns or bridges, for example, can be made in different configurations depending on a variety of criteria. Such criteria include for example the desired aesthetics, costs, preparation time or capabilities of a selected manufacturer.

Many dental restorations are made as a two or more component configuration, with the individual components providing different characteristics for the restoration. A common two-component configuration includes a dental restoration prepared from a framework which is provided with a glazing or a veneer. The framework typically provides the dental restoration with a good mechanical stability and the glazing or the veneer typically provides the dental restoration with the desired good aesthetics. Typically the framework and the glazing/veneer are made of different base materials, for example ceramic and glass-ceramic, each being selected in accordance with the desired function of the respective component.

Other dental restorations are made of a single component only and are often referred to as monolithic dental restorations in the field of dentistry. Such monolithic dental restorations typically are made of one mechanically stable material, for example a ceramic material, and do not have an additional glazing or veneer. In the field of dental technology there is, on the other hand, a general desire to provide a dental restoration with at least a glazing for achieving a pleasant optical appearance.

Monolithic dental ceramic restorations have become relatively common. Such monolithic ceramic restorations may be manufactured from ceramic blocks by grinding. The ceramic material these blocks are made of may be provided at a final stage, for example sintered or cast to final density prior to grinding, so that the dental restoration is ready to use directly after grinding which eventually includes a final polishing step. Suitable ceramic blocks are commercially available at different pre-determined tooth colors so that the desired color of the dental restoration can be determined by selecting a block having the appropriate color.

Alternatively, monolithic ceramic restorations can be made from pre-sintered ceramic blocks. Such pre-sintered ceramic blocks typically have an open-celled material structure, as for example obtainable by pre-sintering a ceramic powder to a stage at which the powder particles adhere to each other but leave voids in between. A precursor of the dental restoration can typically be milled from such a pre-sintered ceramic block and that precursor can be converted into the dental restoration in a sintering step.

Pre-sintered ceramic blocks are often provided without color. The dental restoration can be provided with a desired standardized tooth color by soaking the dental restoration precursor with a so-called coloring solution, as for example disclosed in WO 2014/046949 A1. Alternatively, pre-colored zirconia is available in standardized tooth colors where the coloring agent has already been added during the block production process.

Although current approaches for manufacturing of monolithic dental restorations provide a variety of advantages, there is still a desire for a method allowing the manufacturing of individually colored monolithic dental restorations at a cost efficient manner and at a good aesthetic quality.

DESCRIPTION OF THE INVENTION

The invention relates to a method of making a monolithic dental restoration. The method comprises the step of providing a monolithic precursor of a dental restoration. The monolithic dental restoration precursor is made of zirconia material that has a relative density of greater than 98% of the theoretic density of the zirconia material. The method further comprises the step of firing the monolithic dental restoration precursor to provide the monolithic dental restoration.

The invention is advantageous in that it enables the use of standardized zirconia material for the making of dental restorations in different ways. In particular the invention allows the making of a monolithic dental restoration without a glazing at a color quality that resembles the color quality of a dental restoration with a glazing. Further, the invention allows for eliminating a glazing step in the making of dental restorations and therefore helps minimizing costs in the making of dental restorations. It has been found that the invention further allows for adjusting a color of a dental restoration, for example in case a dental restoration was finished slightly too dark due to color tolerances that usually occur during manufacturing.

The dental restoration precursor and the dental restoration preferably have the same or substantially the same theoretic density.

The zirconia material as referred to in the present specification comprises between 80% and 99% by weight zirconium oxide, and preferably between 85% and 95% by weight zirconium oxide.

For the purpose of the present specification the term "monolithic" with respect to a monolithic piece or item (like the dental restoration or dental restoration precursor) means that the percentage of zirconium oxide of between 80% and 99% by weight, and preferably between 85% and 95% by weight, is present in all macroscopic portions of the monolithic item. In particular, the item preferably does not contain any macroscopic layer made of material having less than 90% of zirconium oxide.

The term "macroscopic" refers to a size of an object which can be perceived with the eye of a person eye without the aid of a magnifying device. Particularly, for the purpose of the present invention an absolute dimension of 0.05 mm is regarded to be a macroscopic dimension.

The zirconia material may further comprise 0-1% by weight aluminum oxide. Further the zirconia material may comprise 0-10% by weight of at least one of hafnium oxide, yttrium oxide and oxides from gallium, germanium, and indium. The zirconia material may also comprise 0.0005 to 1.5% by weight of coloring additives, selected from the group consisting of $Fe_2O_3$, $Tb_4O_7$, $Bi_2O_3$, $Er_2O_3$ and/or $MnO_2$. The zirconia material is preferably selected to be compatible for use in human bodies.

A dental restoration as referred to herein may be selected from at least a dental crown, a partial dental crown and a dental bridge. In particular the dental restoration preferably has a shape which resembles the shape of a natural tooth or teeth.

A dental restoration precursor as referred to herein preferably has a shape which corresponds or substantially corresponds to the shape of the dental restoration. Any differences in shape may arise from very slight distortions or deformations from the firing step (or from slight material removal in a polishing step as described further below). The dental restoration precursor as referred to in this specification may basically differ from the dental restoration by the firing step (and optionally the polishing step) which the dental restoration has additionally undergone in comparison to the dental restoration precursor.

The density of a body for the purpose of the present specification is calculated as follows. The overall volume of the body is determined. The overall volume is the volume defined by the outer surface of the body. Further, the weight of the body is determined. The density is determined by the weight of the body divided by the overall volume of the body.

The relative density of a body is determined by the density of a body divided by the theoretical density of the body. The theoretical density is the density of a non-porous body.

In one embodiment the firing step according to the invention is performed at a temperature of at least about 800° C. Further, the firing step is preferably performed below a temperature of 1100° C. The firing step may be performed for a duration of at least 10 seconds, and preferably at least 1 minute. Further, firing step may be performed for a duration of less than 30 minutes, preferably less than 10 minutes. In a particular example the firing step is performed at a temperature of about 970° C. for a duration of about at least 1 minute. Preferably, two firing steps according to the invention are performed consecutively at a temperature of about 970° C. for a duration of about at least 1 minute and with cooling the monolithic dental restoration precursor between these two firing steps to about 20° C. to 50° C. The firing can be performed in a dental furnace as for example available under the designation DEKEMA Austromat 3001 from the company DEKEMA Dental-Keramiköfen GmbH. Typically each firing step comprises a heating phase, a steady state phase and a cooling phase. Further, the duration of the firing in context of the present specification refers to the duration of the steady state phase. For example the temperature of 970° C. in the embodiment above refers to the temperature of the steady state phase which lasts in the embodiment for 1 minute. The heating phase may be performed at a heating rate within a range of 10° C. per minute to 100° C. per minute, in more particular within a range of 50° C. per minute to 80° C. The cooling phase is typically performed by moving the fired object out of the furnace. Accordingly, the cooling rate may be within a range of 10° C. per minute to 100° C. or greater. Typically the dental furnace is pre-heated to an initial temperature, which in the embodiment is about 500° C.

In an embodiment the method further comprises the step of providing a green body of the monolithic dental restoration precursor. The green body is preferably made of zirconia material having a relative density which is less than 98% of the theoretic density of the zirconia material. More preferably the relative density is between about 40% and about 70%. Further, the green body is preferably has an open-porous material structure. Such an open-porous material structure can be obtained by pre-sintering a body that is preformed from a powder of the zirconia material. The pre-sintering is performed at temperatures and a duration which just causes the powder particles to fuse and/or bond to each other but so that still spaces are present between the powder particles. These spaces form the open-porosity of the material.

The method may further comprise the step of providing the green body by milling or grinding from a blank of zirconia material. Such a method is disclosed for example in WO2014/022643 A1. The method may further comprise the step of providing the green body by building up from a powder material. One method of building up a green body is for example disclosed in WO 2013/181262. The method may further comprise the steps of providing the green body by building up from a powder material and providing the green body by milling or grinding from a blank of zirconia material in combination, as for example disclosed in WO 2012/036852 A1. It is noted that in the prior art the green body (having an open-porous material structure) may sometimes be named dental restoration precursor. However, for the purpose of the present specification the dental restoration precursor has a relative density of greater than 98% and therefore has a material structure that is at least substantially non-porous.

In a further embodiment the method comprises the step of soaking the green body with a coloring liquid. In particular, the step of soaking may be performed by soaking the green body with the coloring liquid. Alternatively, the step of soaking may be performed by soaking the blank with the coloring liquid.

The coloring liquid may be a coloring solution that comprises a solvent, a complexing agent, and a coloring agent. The solvent may be present in an amount of about 30% to about 99% by weight.

The solvent may be selected from the group consisting of water, alcohols or polar aprotic liquids, a polar liquids or mixtures of water with alcohols and/or polar aprotic liquids.

The complexing agent may have Y number of coordinating ligands. The complexing agent may be present in an amount of X1 mol and may have at least 2 coordinating ligands. The complexing agent may be used in an at least stoichiometric ratio with respect to the metal ions present in the coloring agent. The complexing agent may be selected from the group consisting of crown ethers, cryptands, ethylenediaminetriacetate and its salts, ethylenediaminetetraacetate (EDTA) and its salts, nitrilotriacetate (NTA) and its salts, citric acid and its salts, triethylentetramine and porphin.

The coloring agent may comprise metal ions present in an amount of X2 mol. The coloring agent may comprise atoms of the group consisting of rare earth elements and/or of the subgroups of the rare earth elements and/or salts of transition metals of the groups IIIA, IVA, VA, VIA, VIIA, VIIIA, IB and/or IIB. The coloring agent may be a salt comprising metal cations and anions. The anions may be selected from the group consisting of $OAc^-$, $NO_3^-$, $NO_2^-$, $CO_3^-$, $HCO_3^-$, $ONC^-$, $SCN^-$, $SO_4^-$, $SO_3^{2-}$, gluturate, lactate, gluconate, propionate, butyrate, glucuronate, benzoate and phenolate. The coloring solution may comprise less than about 1% by weight of halogen. The coloring agent may comprise metal ions, for example selected from Fe, Mn, Er, Tb, Cr, Bi, Pr, Co in an amount of about 0.1 to about 20% by weight.

The complexing agent is preferably present in an amount sufficient to dissolve the coloring agent in the solvent, and preferably fulfills the equation: $X1/X2*Y>$about 5.5.

The coloring solution may comprise additives in an amount of about 0.1 to about 12% by weight. Such additives may be stabilizers and complex builders, for example.

In a further embodiment the method, further comprises the step of drying the green body soaked with the coloring liquid. The drying is preferably performed at temperatures around normal room temperature, for example at about 20° C. to 23° C., preferably at least at a temperature below 100° C. The skilled person is aware that nevertheless drying can be performed at other temperatures and by use of a variety of techniques, for example red light, vacuum, and/or microwaves.

In an embodiment the method further comprises the step of smoothing the green body. For example, if the green body is milled from a blank of material any significant mill grooves may be smoothened. This avoids that the presence of significant mill grooves on the sintered dental restoration precursor. Because the pre-sintered material has a significantly lower material strength than the sintered material, performing the smoothening step at the pre-sintered green body help minimizing efforts.

In a further embodiment the method further comprises the step of sintering. As a result of the sintering step the monolithic dental restoration precursor is provided. The step of sintering is preferably performed to cause the relative density to be increased to the relative density of greater than 98%.

In one embodiment the method comprises the step of polishing the monolithic dental restoration. The step of polishing the monolithic dental restoration may comprise applying a polishing paste on the dental restoration and polishing the dental restoration by use of the polishing paste and polishing tools. A suitable polishing paste may comprise diamond particles in a size range of less than about 20 μm.

The method of the invention may particularly comprise the above mentioned steps in the following order:
(i) providing a green body of the monolithic dental restoration precursor;
(ii) soaking the green body with a coloring liquid;
(iii) drying the green body soaked with the coloring liquid;
(iv) sintering the green body soaked with the coloring liquid to form the dental restoration precursor;
(v) optionally polishing the dental restoration precursor; and
(vi) firing the optionally polished dental restoration precursor.

Each of the method steps is based on a starting product and results in an end product. By performing the method steps in the order as specified above the end product of each step (i), (ii), (iii), (iv) and (v) forms the starting product for the steps (ii), (iii), (iv), (v) and (vi) respectively. In case the polishing step is omitted, the end product of the step (iv) forms the starting product of the step (vi).

In one embodiment method of the invention may particularly comprise the above mentioned steps in the following order:
(i) providing a green body of the monolithic dental restoration precursor;
(ii) sintering the green body to form the dental restoration precursor;
(iii) optionally polishing the dental restoration precursor; and
(iv) firing the optionally polished dental restoration precursor.

In this embodiment the green body may have the desired color or coloring (for example a color gradation). Again by performing the method steps in the order as specified the end product of each step (i), (ii) and (iii) forms the starting product for the steps (ii), (iii) and (iv), respectively. In case the polishing step is omitted, the end product of the step (ii) forms the starting product of the step (iv).

Generally, the method of the invention comprises a firing step which is performed on an already substantially fully dense (relative density>98%) zirconia material (the dental restoration precursor). It has been found that the firing of such dense material causes the color of the zirconia material to slightly change. In particular, the sintering of such dense material causes the appearance to change toward an appearance that is normally expected only from dental restorations having a glazing, although the dental restoration of the present invention does not have any glazing. In this respect a glazing is regarded as a coating made of a glass material.

BRIEF DESCRIPTION OF THE FIGURES

FIG. 1 shows a diagram illustrating the results of color measurements of Examples including an Example obtained by a method according to an embodiment of the invention.

EXAMPLES

Six zirconia anterior crowns were milled from Lava™ Plus high translucency zirconia blocks (available from 3M Deutschland GmbH, #679670, multi XL block size). The crowns were removed from the holding device with a turbine handpiece and the area of the holding pins were smoothened with a P2500 grits grain sandpaper. The crowns were assorted into three groups of two crown each:

Group A: crowns for finishing by a glazing

Group B: crowns for finishing by only polishing

Group C: crowns for finishing by polishing and subsequently firing

The outer surfaces of the crowns of groups B and C were smoothened with the sandpaper (P2500 grits) for facilitating the polishing after sintering.

Coloring

All six crowns were soaked for two minutes with Lava™ Plus high translucency dyeing liquid A3 (available from 3M Deutschland GmbH, #515601), air-dried at room temperature 23° C. and fired at 1450° C. for 2 hours in a Lava™ Furnace 200 oven available from 3M Deutschland GmbH.

Firing/Finishing

Comparative Example 1

The crowns of group A were glazed with a dental glaze material (VITA AKZENT Plus; #A0764 from the company Vita Zahnfabrik H. Rauter GmbH & Co. KG) and fired twice at 970° C. for 1 minute in a dental furnace (DEKEMA Austromat 3001 from the company DEKEMA Dental-Keramiköfen GmbH). In each of the firing steps the dental furnace was pre-heated to 500° C. The crowns were placed on a firing support at room temperature (23° C.) and moved into the furnace. The furnace was then heated at a heating rate of 80° C. per minute to a temperature of 970° C. The temperature was maintained at 970° C. while the crowns were fired at that temperature for 1 minute before the crowns were moved outside the dental furnace for cooling toward room temperature.

Comparative Example 2

The crowns of group B were polished with dental polishing paste (Fino carat plus II).

Example 3 According to the Invention

The crowns of group C were polished with dental polishing paste (Fino carat plus II) and fired twice after polishing. The additional firing steps were performed at 970° C. for 1 minute.

The firing steps performed for crowns of groups A and C therefore were the same, although the crowns of group C were not provided with any glazing.

Color Measurement

All crowns were measured with a photospectrometer that is available under the designation Vita Easyshade® Advance, from Vita Zahnfabrik, Germany. The Vita Easyshade® Advance can be used to measure color differences, for example between different objects. The difference is measured in the form of a so-called Delta E value. A higher Delta E value represents a greater color difference than a lower Delta E. The crowns of group A were used as reference.

FIG. 1 is a diagram which represents a color deviation on the vertical axis based on the Delta E metrics. The zero value represents the color value of the reference samples (crowns of group A). The diagram further illustrates the color deviation of the crowns of groups B in relation to the reference color (group A) and the color deviation of the crowns of group C in relation to the reference color (group A).

The visual appearance of the crowns of group B (finished by polishing only) is significantly different than the visual appearance of the crowns of group A. The measuring results of the color measurement of the crowns of group A and the crowns of group B confirm, that the colors of group A and B significantly deviate. In particular, the crowns of group B appear more dark or gray, compared to the crowns of group A (finished by glazing). This color deviation had to be accepted in case zirconia material was used to make dental restorations without glazing. Therefore there has been a general tradeoff between, on the one hand, applying the additional step of glazing in the manufacturing of dental restorations and, on the other hand, the achievement of color precision. Although this tradeoff can be mitigated by selecting differently colored zirconia materials there is a general desire to use one zirconia material for different manufacturing techniques (glazing optional).

The invention allows minimizing the color deviation between dental restorations that are finished by a glazing and dental restorations that do not have a glazing but are just polished. This is illustrated in the diagram for the crowns of group C. As apparent from the diagram the color difference between the crowns of group A and group C is significantly smaller than the color difference between the crowns of group A and group B. The only difference between the crowns of group C and B is the additional firing step applied to the crowns of group C.

The invention claimed is:

1. A method of making a monolithic dental restoration, comprising:
    providing a green body monolithic precursor of a dental restoration;
    sintering the green body to provide a monolithic precursor of a dental restoration being made of zirconia material having a relative density of greater than 98% of the theoretic density of the zirconia material;
    polishing the monolithic dental restoration precursor; and
    firing the monolithic dental restoration precursor at a temperature of at least 800° C. for a duration of at least 10 seconds to provide the monolithic dental restoration, wherein the monolithic dental restoration precursor does not have a glazing;
    wherein the firing step comprises a heating phase, a steady state phase, and a cooling phase, and wherein the steady state phase is performed for a duration of less than 10 minutes, wherein the duration of the firing refers to the duration of the steady state phase.

2. The method of claim 1, wherein zirconia material comprising between 85% by weight and 95% by weight $ZrO_2$.

3. The method of claim 1 wherein the green body is made of zirconia material having a relative density which is between about 40% and about 70% of the theoretic density of the zirconia material.

4. The method of claim 3, further comprising providing the green body by milling or grinding from a blank of zirconia material.

5. The method of claim 3, further comprising soaking the green body with a coloring liquid.

6. The method of claim 5, further comprising drying the green body soaked with the coloring liquid.

7. The method of claim 3, further comprising smoothing the green body.

8. The method of claim 1, comprising providing the monolithic dental restoration precursor in a pre-colored form.

9. The method of claim 1, wherein the step of sintering causes the relative density to be increased to the relative density of greater than 98%.

10. The method claim 1, wherein the step of polishing the monolithic dental restoration precursor comprises applying a polishing paste on the monolithic dental restoration precursor and polishing the monolithic dental restoration precursor by use of the polishing paste and a polishing tool.

11. The method of claim 8, wherein the pre-colored dental restoration precursor is made of a zirconia material comprising between about 5% by weight to 10% by weight yttrium oxide, $Er_2O_3$, $Tb_4O_7$, $Bi_2O_3$, MnO, and $Fe_2O_3$; and wherein $Er_2O_3$ is present in an amount up to about 1% by weight, $Tb_4O_7$ is present in an amount up to about 1% by weight, $Bi_2O_3$ is present in an amount up to about 0.3% by weight, MnO is present in an amount up to about 0.05%, and $Fe_2O_3$ is present in an amount up to about 0.5% by weight.

\* \* \* \* \*